United States Patent [19]

Wu

[11] Patent Number: 5,358,919
[45] Date of Patent: Oct. 25, 1994

[54] PREPARATION AND USE OF ISOMERIZATION CATALYSTS

[75] Inventor: An-hsiang Wu, Bartlesville, Okla.

[73] Assignee: Phillips Petroleum Company, Bartlesville, Okla.

[21] Appl. No.: 131,042

[22] Filed: Oct. 1, 1993

Related U.S. Application Data

[62] Division of Ser. No. 12,662, Feb. 3, 1993, Pat. No. 5,292,988.

[51] Int. Cl.$^5$ .............................. B01J 27/122
[52] U.S. Cl. ................... 502/225; 502/224; 502/226; 502/229; 502/231
[58] Field of Search ............ 502/225, 224, 229, 231, 502/226

[56] References Cited

U.S. PATENT DOCUMENTS

| | | | |
|---|---|---|---|
| 2,820,074 | 1/1958 | Pines | 260/683.49 |
| 2,963,528 | 12/1960 | Schwartz | 585/745 |
| 3,238,272 | 3/1966 | Nixon | 260/683.65 |
| 3,248,343 | 4/1966 | Kelly et al. | 252/442 |
| 3,420,909 | 1/1969 | Schmerling | 260/671 |
| 3,502,735 | 3/1970 | Copelin | 260/658 |
| 3,523,072 | 8/1970 | Schneider | 585/743 |
| 3,631,211 | 12/1971 | Schmerling | 260/668 C |
| 3,655,797 | 4/1972 | Schmerling | 260/671 |
| 3,846,503 | 11/1974 | Schmerling et al. | 260/666 P |
| 5,004,859 | 4/1991 | Schmidt et al. | 85/741 |
| 5,202,519 | 4/1993 | Khare | 585/741 |
| 5,219,817 | 6/1993 | McDaniel et al. | 502/231 |
| 5,221,655 | 6/1993 | McDaniel et al. | 502/228 |
| 5,238,896 | 8/1993 | Khare | 502/172 |
| 5,254,794 | 10/1993 | Wu | . |
| 5,292,988 | 3/1994 | Wu | 585/741 |

OTHER PUBLICATIONS

N. Kitajima, "Two Component Friedel-Crafts Catalysts as Solid Superacids", Materials Chemistry and Physics 17 (1987), pp. 31–48.

N. Kitajima et al., "Cu(AlCl$_4$)$_2$ as a Catalyst for the Isomerization of Pentane at Room Temperature", Journal of Molecular Catalysis 10 (1981), pp. 121–122.

Y. Ono et al., "Isomerization of Pentane with AlCl$_3$–CuSo$_4$ Mixtures", Journal of Catalysis 64 (1980), pp. 13–17.

N. Kitajima et al., "On the Active Species of Aluminum(III) Bromide-Copper(II) Bromide Mixtures as Catalysts for the Isomerization of Pentane", Journal Chem. Society, Perkin Transactions II, 1980, pp. 1201–1205.

Y. Ono et al., "Isomerization of Pentane with Aluminum Chloride (Gallium Chloride)-Cupric Salt Complexes", Proceedings 7th Internat. Congress Catalys., Tokyo, 1980, pp. 1006–1017.

Y. Ono et al., "Highly Selective Isomerization of Pentane with AlBr$_3$–Metal Sulfate Mixtures", Chemistry Letters, 1978, pp. 1061–1064.

Primary Examiner—Anthony McFarlane
Attorney, Agent, or Firm—K. K. Brandes

[57] ABSTRACT

Novel compositions, being effective as catalysts for alkane and/or cycloalkane isomerization, are prepared by a method which includes the steps of impregnating alumina with a sulfate of at least one metal selected from the group consisting of copper, iron, cobalt, nickel, manganese, zinc and magnesium, calcining the thus-obtained impregnated alumina materials, and heating the calcined materials with AlCl$_3$ and at least one chlorinated hydrocarbon (preferably CCl$_4$) at a temperature of about 40°–90° C. Preferably, this method also includes a step of treating the calcined impregnated alumina materials with gaseous hydrogen chloride before the heating with AlCl$_3$ and the chlorinated hydrocarbon(s) is carried out.

20 Claims, No Drawings

PREPARATION AND USE OF ISOMERIZATION CATALYSTS

BACKGROUND OF THE INVENTION

This is a division of application Ser. No. 08/012,662, filed Feb. 3, 1993, now U.S. Pat. No. 5,292,988.

In one aspect, this invention relates to the preparation of materials which are active as alkane/cycloalkane isomerization catalysts, In another aspect, this invention relates to time use of materials prepared by methods of this invention as catalysts for isomerizing cycloalkanes. In a further aspect, this invention relates to the use of materials prepared by methods of this invention as catalysts for isomerizing alkanes.

The use of combinations of aluminum chloride and certain metal sulfates and chlorides (in particular $CuSO_4$ and $CuCl_2$) for alkane isomerization is known and has been described in various scientific articles. The present invention Is directed to the preparation of catalyst materials from aluminum chloride, certain metal sulfates and/or chlorides, and a specific inorganic support material. These novel catalyst compositions can be used as solid isomerization catalysts, e.g., in fixed catalyst bed operations for isomerizing cycloalkanes and/or alkanes.

SUMMARY OF THE INVENTION

It is an object of this invention to prepare catalyst materials from aluminum chloride, certain metal sulfates and/or chlorides and a specific inorganic support material. It is another object of this invention to employ materials prepared by methods of this invention as catalysts for the isomerization of cycloalkanes. It is a further object of this invention to employ materials prepared by methods of this invention as catalysts for the isomerization of alkanes. Other objects and advantages will be apparent from the detailed description of the invention and the appended claims.

In accordance with this invention, a composition of matter is prepared by a method comprising the steps of:

(1) impregnating alumina having a surface area (measured by the BET method employing $N_2$) of at least about 40 m²/g with a solution of at least one metal salt selected from the group consisting of copper(II) sulfate, copper(II) chloride, iron(II) sulfate, cobalt (II) sulfate, cobalt(II) chloride, nickel(II) sulfate, nickel(II) chloride, manganese(II) sulfate, zinc sulfate and magnesium sulfate;

(2) calcining the material obtained in step (1) for a period of at least 0.5 hour at a temperature of about 400°–700° C.;

(3) heating for a period of at least one hour, at a temperature in the range of about 40° C. to about 90° C. and in substantial absence of water, the calcined material obtained in step (2) with aluminum chloride and at least one chlorinated hydrocarbon (i.e., chlorine derivative of a hydrocarbon) having a normal boiling point (i.e., boiling point at a pressure of about 1 atm) of about 40°–90° C., wherein the weight ratio of $AlCl_3$ to said calcined material obtained in step (2) is at least about 0.35: 1; and (4) separating the solid material contained in the reaction mixture formed in step (3) from said at least one chlorinated hydrocarbon under a dry gas atmosphere.

Preferably, the above-described preparation method comprises the additional step of (2a) contacting the calcined material obtained in step (2) with hydrogen chloride gas for at least about 10 minutes, wherein step (3) is carried out with the HCl-treated calcined material obtained in step (2a). Another preferred embodiment comprises the additional step of (1a) substantially drying the material obtained in step (1) at a temperature below about 400° C. (more preferably at about 50°–150° C. and a pressure below about 1 atm.), wherein step (2) is carried out with the substantially dried material obtained in step (1a).

Also in accordance with this invention, a cycloalkane conversion process comprises contacting, at a temperature of up to about 100° C. (preferably about 20°–50° C.), at least one cycloalkane containing 5–10 carbon atoms per molecule with at least one of the isomerization catalyst compositions having been prepared by the above-outlined preparation method comprising steps (1), (2), (3) and (4), at effective isomerization conditions so as to substantially convert said at least one feed cycloalkane to at least one product cycloalkane isomer (having the same number of carbon atoms per molecule as said at least one feed cycloalkane but having a different structural formula). Preferably, the feed cycloalkane is methylcyclopentane, and the product cycloalkane is cyclohexane. Also, preferably, the cycloalkane isomerization process of this invention is carried out with a catalyst obtained by the preparation method comprising the additional step (2a) before step (3), as described above.

Further in accordance with this invention, an alkane conversion process comprises the step of contacting, at a temperature of up to about 100° C. (preferably about 20°–50° C.), at least one feed alkane (i.e., at least one normal alkane or at least one isoalkane or a mixture thereof) containing about 4–10 carbon atoms per molecule with at least one of the isomerization catalyst compositions having been prepared by the above-outlined preparation method comprising steps (1), (2), (3) and (4), wherein the at least one dissolved metal salt employed in step (1) is selected from the group consisting of dissolved copper(II) sulfate and nickel(II) sulfate, at effective isomerization conditions so as to convert a portion of said at least one feed alkane to at least one product alkane isomer (having the same number of carbon atoms per molecule as said at least one feed alkane but having a different structural formula). Preferably, the feed alkane is n-pentane or isopentane (2-methylbutane).

Still further in accordance with this invention, a hydrocarbon conversion process comprises the step of contacting, at a temperature of up to about 100° C. (preferably about 20 –50° C.) at least one feed alkane selected from the group consisting of normal alkanes and isoalkanes containing about 4–10 carbon atoms per molecule, or alternatively, at least one feed cycloalkane containing 5–10 carbon atoms per molecule with at least one of the isomerization catalyst compositions having been prepared by the above-outlined preparation method comprising steps (1), (2) , (2a) , (3) and (4), at effective isomerization conditions as to convert a portion of said at least one feed alkane to at least one product alkane isomer (having the same number of carbon atoms per molecule as said at least one feed alkane) or, alternatively, substantially convert said at least one feed cycloalkane to at least one product cycloalkane (having the same number of carbon atoms per molecule as said at least one feed cycloalkane but having a different structural formula). Preferably, the feed alkane is n-pentane or isopentane (2-methylbutane). Also preferably, the feed cycloalkane is methylcyclopentane.

DETAILED DESCRIPTION OF THE INVENTION

Step (1) of the preparation method of this invention can be carried out by any suitable means. Generally, alumina particles (such as pellets, cylindrical extrudates, trilobal particles), which preferably have a particle size of about 20 to about 200 mesh (preferably about 20–40 mesh), a surface area (determined by the BET method of Brunauer, Emmett and Teller employing nitrogen) of about 200 to about 500 $m^2/g$, and a pore volume (determined by water intrusion at about 1 atm) of about 0.6 to about 0.8 $cm^3/g$, are impregnated with an aqueous solution of at least one of the metal salts listed above (i.e., $CuSO_4$, $CuCl_2$, $FeSO_4$, $CoSO_4$, $CoCl_2$, $NiSO_4$, $NiCl_2$, $MnSO_4$, $ZnSO_4$, $MgSO_4$). Generally, the concentration of the at least one metal sulfate and/or chloride in the impregnating solution is about 0.1–3.0 mol/l, preferably about 0.5–2.0 mol/l. It is within the scope of this invention, yet presently not preferred, to have $SiO_2$ or $AlPO_4$ (up to about 30 weight-%) present in the alumina particles. Generally, the alumina particles are impregnated by completely submerging them in the aqueous metal salt solution.

Preferably, the impregnated alumina particles obtained in step (1) are then dried in step (1a), more preferably at a temperature of about 50°–150° C. under vacuum conditions for a period of about 0.5–20 hours. The impregnated alumina particles obtained in step (1), or preferably in step (1a), are then calcined in step (2) at a temperature in the range of about 400° C. to about 750° C. (preferably at about 500°–700° C. for about 1–5 hours), either in a free oxygen-containing atmosphere (such as air) or in an inert gas atmosphere (such as $N_2$, He, Ar and the like).

The calcined particles obtained in step (2) are allowed to cool and are then mixed and heated in step (3) with $AlCl_3$ and at least one chlorinated hydrocarbon, under reflux conditions in a dry inert gas atmosphere at a temperature of about 40°–90° C., preferably about 70°–80° C., for a time period of about 4 to about 120 hours, preferably about 10–30 hours, more preferably 15–25 hours. It is preferred to carry out step (3) with agitation, either mechanically (e.g., by means of a stirrer) or ultrasonically. In step (3), the weight ratio of $AlCl_3$ to the calcined particles is preferably about 0.37:1 to 1.0:1.

One chlorinated hydrocarbon or a mixture of two or more chlorinated hydrocarbons having a normal boiling point in the range of about 40°–90° C., preferably about 70°–80° C. can be employed as agent (d) in step (3). Preferred chlorinated hydrocarbons are chlorinated paraffins (alkanes). Non-limiting examples of agent (d) include dichloromethane, chloroform (trichloromethane), carbon tetrachloride, 1,1-dichloroethane, 1,2-dichloroethane, 1,1,1-trichloroethane, 1,1-dichloropropane, 2,2-dichloropropane, 1-chlorobutane, 2-chloro-2-methylbutane, and mixtures thereof. The presently more preferred chlorinated hydrocarbon is carbon tetrachloride. Generally, the ratio of the weight of the at least one chlorinated hydrocarbon to the combined weight of $AlCl_3$ and the calcined particles (obtained in step 2) is about 4:1 to about 20:1.

Preferably, the calcined particles obtained in step (2) are first contacted in step (2a) with dry gaseous hydrogen chloride (generally a dry mixture of HCl and an inert gas such as $N_2$, He, Ar and the like, preferably having a HCl concentration of 4–60 volume-%) before step (3) is carried out. Generally, the exposure to the HCl-containing gas in this step (2a) is carried out for at least 10 minutes, preferably about 1–10 hours at a temperature of about 600°–750° C. (more preferably about 700°–750° C.), generally at atmospheric pressure conditions. If step (2a) is carried out, the subsequent step (3) employs the material obtained in step (2a).

Separation step (4) can be carried out in any suitable manner. Preferably, the finished reaction mixture of step (3) is filtered, and the solid filter cake is then substantially dried at any suitable conditions, preferably at subatmospheric (i.e., vacuum) conditions, at a temperature of about 25°–60° C. Preferably, step (4) is carried out under a dry inert gas atmosphere ($N_2$, He, Ar and the like). The finished/dried catalyst particles should be stored under a dry inert gas atmosphere.

In one embodiment of this invention, the catalyst composition described above are employed for isomerizing $C_5$–$C_{10}$ cycloalkanes, preferably methyl-substituted cycloalkanes. Nonlimiting examples of suitable feed cycloalkanes are methylcyclobutane, methylcyclopentane, 1,1-dimethylcyclopentane, 1,2-dimethylcyclopentane, 1,3-dimethylcyclopentane, methylcyclohexane, 1,1-dimethylcyclohexane, 1,2-dimethylcyclohoxane, 1,3-dimethylcyclohexane, ethylcyclohexane, methylcycloheptane, 1,methyl-2-ethylcyclopentane, 1,1-dimethylcycloheptane, 1,2-dimethylcycloheptane, 1,3-dimethylcycloheptane, ethylcycloheptane, 1-methyl-2-ethylcyclohexame, methylcyclooctane, 1,1-dimethylcyclooctane, 1,2-dimethylcyclooctane, 1,3-dimethylcyclooctane, and mixture thereof. The preferred cycloalkane is methylcyclopentane which is substantially converted to cyclohexane in accordance with the process of this invention. Preferably the catalyst particles are prepared by the method which includes step (2a).

In another embodiment of this invention, the catalyst composition described above is employed for partially isomerizing (and partially disproportionating) normal (straight chain) alkanes and isoalkanes (i.e., branched) alkanes containing 4–10 carbon atoms per molecule. Non-limiting examples of suitable alkanes are n-butane, isobutane, n-pentane, isopentane (i.e., 2-methylbutane), n-hexane, isohexanes (such as 2-methylpentane, 3-methyl-yl-pentane, 2,2-dimethylbutane), n-heptane, isoheptanes (in particular methyl-substituted hexanes and dimethyl-substituted pentanes, n-octane, isooctanes (in particular methyl-substituted heptanes and dimethyl-substituted hexanes), n-nonane, isononanes (in particular methyl-substituted octanes, dimethyl-substituted heptanes, trimethyl-substituted hexanes), n-decane and isodecanes (in particular methyl-substituted nonanes, dimethyl-substituted octanes, trimethyl-substituted heptanes, tetramethyl-substituted hexanes). Presently preferred are $C_4$–$C_8$ n-alkanes and $C_4$–$C_8$ isoalkanes, such as those present in commercial alkylation products (i.e., products obtained by the reaction of an isoalkane such as isobutane with an alkene such as butene-2). Particularly preferred feed alkanes are n-pentane and isopentane (2-methylbutane). Preferably, the catalyst particles are prepared by the method which includes step (2a).

The process for isomerizing $C_4$–$C_{10}$ cycloalkanes and/or $C_5$–$C_{10}$ alkanes with one of the above-described catalyst compositions can be carried out under any suitable reaction conditions at a relatively low temperature of up to about 100° C., more preferably about 20–50° C., most preferably about 30°–40° C., generally at 1-5 arm pressure. The feed alkane and/or cycloalkane can be contacted with the catalyst composition in any suitable mode, such as in a slurry-type operation in which the catalyst is dispersed in the feed alkane and/or cycloalkane, or in a fixed catalyst bed operation in which a feed hydrocarbon stream flows upward or downward through a solid catalyst layer (or several catalyst layers). The time of contact between the feed alkane and/or cycloalkane and the catalyst composition generally is in the range of about 5 minutes to about 8 hours, preferably about 1-2 hours. The isomerization process can be carried out as a batch operation or, preferably, as a continuous operation. Moisture is to be substantially absent during the isomerization process. When feed alkanes are employed, it is quite common that concurrently with the isomerization of a portion of feed alkane(s), another portion of feed alkane(s) is disproportionated, i.e., converted to a mixture of at least one alkane having a higher number of carbon atoms per molecule and at least one alkane having a lower number of carbon atoms per molecule than the feed alkane(s).

The isomerization processes of this invention frequently generate a multitude of products, especially in the case of alkanes which do not only partially isomerize but also, often to a substantial extent, disproportionate to higher and lower alkanes. Thus, it is generally necessary to separate the various formed hydrocarbon products from one another and from unconverted feed hydrocarbons. This separation can be carried out in any suitable manner, generally by fractional distillation (possibly in the presence of an extractant, i.e. , by extractive distillation) as is easily determined by persons skilled in the various liquid-liquid separation technologies.

The following examples are provided to further illustrate the processes of this invention, and are not to be construed as unduly limiting the scope of this invention.

EXAMPLE I

This examples illustrates the preparation of catalyst materials which were used cycloalkane and alkane isomerization tests.

Cataylsts A1-A4 (Control) were prepared by heating various amounts of dry $AlCl_3$, 2.50 grams of 60-200 mesh alumina (calcined at 500° C. for 4 hours; 1/16" extrudates having a surface area of 281 $m^2/g$ and a pore volume of 0.73 cc/g; marketed by Akzo Chemicals, Inc., Chicago, Ill. under the "Ketjen" tradename) and 30 mL dry $CCl_4$ in a dry nitrogen gas atmosphere for 10 hours under reflux conditions. The heated slurry was allowed to cool, filtered, and dried for several hours under vacuum conditions. The amounts (in grams) of $AlCl_3$ per gram $Al_2O_3$ for the four control catalysts were as follows: 0.25 g $AlCl_3$ for preparing Catalyst A1, 0.37 g $AlCl_3$ for preparing Catalyst A2, 0.43 g $AlCl_3$ for preparing Catalyst A3, and 0.50 g $AlCl_3$ for preparing Catalyst A4.

Control Catalysts A5-A8 are essentially duplicates of Catalysts A1-A4.

Catalysts B1 through B4 were prepared as follows. 25 grams of alumina extrudates (described above) were soaked (submerged) in 50 mL of an aqueous, 0.1 molar $CuSO_4$ solution. After about 30 minutes, the $CuSO_4$-impregnated alumina particles were separated from the solution by filtration and calcined at 400° C. for 2 hours. The calcined particles were then heated with dry $AlCl_3$ and dry $CCl_4$, separated and dried, as described for Catalysts A1-A4. The amounts (in grams) of $AlCl_3$ per gram $CuSO_4$-impregnated alumina were 0.25 g (Catalyst B1), 0.37 g (Catalyst B2), 0.43 g (Catalyst B3) and 0.50 g (Catalyst B4).

Catalysts C1-C4 were prepared essentially in accordance with the preparation procedure for Catalysts B1-B4, except that the alumina particles had been soaked in a 0.2 molar $CuSO_4$ solution before the heating with $AlCl_3$ and $CCl_4$.

Catalysts D1-D4 were prepared essentially in accordance with the preparation procedure for Catalysts B1-B4, except that the alumina particles had been soaked in a 0.5 molar $CuSO_4$ solution before the heating with $AlCl_3$ and $CCl_4$.

Catalysts E1-E4 were prepared essentially in accordance with the preparation procedure for Catalysts B1-B4, except that the alumina particles had been soaked in a 1.0 molar $CuSO_4$ solution before the heating with $AlCl_3$ and $CCl_4$.

Catalysts F1-F4 were prepared essentially in accordance with the preparation procedure for Catalysts B1-B4, except that the alumina particles had been soaked in a 1.5 molar $CuSO_4$ solution before the heating with $ACl_3$ and $CCl_4$.

Catalysts G1-G4 were prepared essentially in accordance with the preparation procedure for Catalysts B1-B4 except that the alumina particles had been soaked in a 0. 1 molar solution of $CuCl_2$ (in lieu of $CuSO_4$) before the heating with $AlCl_3$ and $CCl_4$.

Catalysts H1-H4 were prepared essentially in accordance with the preparation procedure for Catalysts B1-B4, except that the alumina particles had been soaked in a 0.2 molar $CuCl_2$ solution before the heating with $ACl_3$ and $CCl_4$.

Catalysts I1-I4 were prepared essentially in accordance with the preparation procedure for Catalysts B1-B4, except that the alumina particles had been soaked in a 0.5 molar $CuCl_2$ solution before the heating with $AlCl_3$ and $CCl_4$.

Catalysts J1-J4 were prepared essentially in accordance with the preparation procedure for Catalysts B1-B4, except that the alumina particles had been soaked in a 1.0 molar $CuCl_2$ solution before the heating with $ACl_4$ and $CCl_4$.

Catalysts L1-L4 were prepared essentially in accordance with the preparation procedure for Catalysts B1-B4, except that the alumina particles had been soaked in a 1.5 molar $CuCl_2$ solution before the heating with $AlCl_3$ and $CCl_4$.

Catalysts L1-L4 were prepared essentially in accordance with the preparation procedure for Catalysts B1-B4, except that the alumina particles had been soaked in a 2.0 molar $CuCl_2$ solution before the heating with $AlCl_3$ and $CCl_4$.

Catalysts M1-M4 were prepared essentially in accordance with the preparation procedure for Catalysts B1-B4, except that the alumina particles had been soaked in a 2.5 molar $CuCl_2$ solution before the heating with $AlCl_3$ and $CCl_4$.

Catalysts N1-N4 were prepared essentially in accordance with the procedure for Catalysts B1-B4, except that the alumina particles had been soaked in a 3.0 molar $CuCl_2$ solution before the heating with $AlCl_3$ and $CCl_4$.

Catalysts O1-O6 were prepared essentially in accordance with the procedure for Catalysts B1, except that the alumina particles had been soaked in a 1.0 molar solution of $FeSO_4$, $CoSO_4$, $NiSO_4$, $MnSO_4$, $ZnSO_4$ and $MgSO_4$, respectively, before tile heating with $ACl_4$ and $CCl_4$.

Catalysts P1–P6 were prepared essentially in accordance with the preparation procedure for Catalyst B3, except that the alumina particles had been soaked in a 1.0 molar solution of $FeSO_4$, $CoSO_4$, $NiSO_4$, $MnSO_4$, $ZnSO_4$ and $MgSO_4$, respectively, before the heating with $AlCl_3$ and $CCl_4$.

Catalysts Q1–Q6 were prepared essentially in accordance with the preparation procedure for Catalyst B3, except that the alumina particles had been soaked in a 1.0 molar solution of $FeSO_4$, $CoSO_4$, $NiSO_4$, $MnSO_4$, $ZnSO_4$ and $MgSO_4$, respectively, before the heating with $ACl_3$ and $CCl_4$, and that the number of grams of $AlCl_3$ per gram impregnated alumina was 0.60.

Catalysts R1–R6 were prepared essentially in accordance with the preparation procedure for Catalyst B3, except that the alumina particles had been soaked in a 1.0 molar solution of $FeSO_4$, $CoSO_4$, $NiSO_4$, $MnSO_4$, $ZnSO_4$ and $MgSO_4$, respectively, before the heating with $AlCl_3$ and $CCl_4$, and that the number of grams of $AlCl_3$ per gram impregnated alumina was 1.0.

EXAMPLE II

This example illustrates the use of the catalyst compositions described in Example I for the isomerization of methylcyclopentane to cyclohexane, at a reaction temperature of about 38°–40° C. 0.51 grams of a dry, finished catalyst composition (to be tested) and 10 mL of dry methylcyclopentane were placed in a sealed glass flask at atmospheric pressure (1 atm.) with slight agitation. After a reaction time of about 1 hour, the flask content was analyzed by means of a gas chromatograph. Tests are summarized in Table I.

TABLE I

| Employed Catalyst | Catalyst Preparation Method | | | | % Conversion of Methylcyclopentane |
|---|---|---|---|---|---|
| | Support | Metal Salt Used to Treat Support | Conc. of Metal Salt in Treating Solution | Grams $AlCl_3$ per Gram treated Support | |
| A1 | $Al_2O_3$ | None | 0 | 0.25 | 4.7 |
| B1 | " | $CuSO_4$ | 0.1 Molar | " | 9.1 |
| C1 | " | " | 0.2 Molar | " | 1.9 |
| D1 | " | " | 0.5 Molar | " | 9.4 |
| | " | " | 1.0 Molar | " | 2.7 |
| A2 | $Al_2O_3$ | None | 0 | 0.37 | 5.9 |
| B2 | " | $CuSO_4$ | 0.1 Molar | " | 10.1 |
| C2 | " | " | 0.2 Molar | " | 24.6 |
| D2 | " | " | 0.5 Molar | " | 29.7 |
| E2 | " | " | 1.0 Molar | " | 41.4 |
| F2 | " | " | 1.5 Molar | " | 31.4 |
| A3 | $Al_2O_3$ | None | 0 | 0.43 | 6.4 |
| C3 | " | " | 0.2 Molar | " | 23.3 |
| D3 | " | " | 0.5 Molar | " | 32.8 |
| E3 | " | " | 1.0 Molar | " | 58.4 |
| F3 | " | " | 1.5 Molar | " | 57.4 |
| A4 | $Al_2O_3$ | None | 0 | 0.50 | 6.7 |
| B4 | " | $CuSO_4$ | 0.1 Molar | " | 8.0 |
| C4 | " | " | 0.2 Molar | " | 20.9 |
| D4 | " | " | 0.5 Molar | " | 23.5 |
| E4 | " | " | 1.0 Molar | " | 40.4 |
| F4 | " | " | 1.5 Molar | " | 46.9 |
| A5 | $Al_2O_3$ | None | 0 | 0.25 | 2.0 |
| G1 | " | $CuSO_4$ | 0.1 Molar | " | 8.4 |
| H1 | " | " | 0.2 Molar | " | 2.9 |
| I1 | " | " | 0.5 Molar | " | 6.6 |
| J1 | " | " | 1.0 Molar | " | 4.6 |
| K1 | " | " | 1.5 Molar | " | 1.4 |
| L1 | $Al_2O_3$ | $CuCl_2$ | 2.0 Molar | 0.25 | 1.4 |
| M1 | " | " | 2.5 Molar | " | 0.8 |
| N1 | " | " | 3.0 Molar | " | 2.0 |
| A6 | $Al_2O_3$ | None | 0 | 0.43 | 4.3 |
| G2 | " | $CuSO_4$ | 0.1 Molar | " | 13.8 |
| H2 | " | " | 0.2 Molar | " | 10.5 |
| I2 | " | " | 0.5 Molar | " | 32.5 |
| J2 | " | " | 1.0 Molar | " | 43.8 |
| K2 | " | " | 1.5 Molar | " | 26.2 |
| L2 | " | " | 2.0 Molar | " | 17.8 |
| M2 | " | " | 2.5 Molar | " | 15.1 |
| N2 | " | " | 3.0 Molar | " | 16.0 |
| A7 | $Al_2O_3$ | None | 0 | 0.60 | 4.5 |
| G3 | " | $CuSO_4$ | 0.1 Molar | " | 11.9 |
| H3 | " | " | 0.2 Molar | " | 10.1 |
| I3 | " | " | 0.5 Molar | " | 26.5 |
| J3 | " | " | 1.0 Molar | " | 37.9 |
| K3 | " | " | 1.5 Molar | " | 45.1 |
| L3 | " | " | 2.0 Molar | " | 49.0 |
| M3 | " | " | 2.5 Molar | " | 30.5 |
| N3 | " | " | 3.0 Molar | " | 46.9 |
| A8 | $Al_2O_3$ | None | 0 | 1.0 | 3.0 |
| G4 | " | $CuSO_4$ | 0.1 Molar | " | 5.9 |
| H4 | " | " | 0.2 Molar | " | 8.7 |
| I4 | " | " | 0.5 Molar | " | 21.1 |
| J4 | " | " | 1.0 Molar | " | 20.2 |
| K4 | " | " | 1.5 Molar | " | 29.5 |
| L4 | " | " | 2.0 Molar | " | 33.4 |
| M4 | " | " | 2.5 Molar | " | 45.3 |
| N4 | " | " | 3.0 Molar | " | 53.4 |
| A5 | $Al_2O_3$ | None | 0 | 0.25 | 2.0 |

TABLE I-continued

| Employed Catalyst | Catalyst Preparation Method | | | | % Conversion of Methylcyclopentane |
|---|---|---|---|---|---|
| | Support | Metal Salt Used to Treat Support | Conc. of Metal Salt in Treating Solution | Grams AlCl$_3$ per Gram treated Support | |
| O1 | " | FeSO$_4$ | 1.0 Molar | " | 1.6 |
| O2 | " | CoSO$_4$ | " | " | 5.7 |
| O3 | " | NiSO$_4$ | " | " | 7.3 |
| O4 | " | MnSO$_4$ | " | " | 2.2 |
| O5 | " | ZnSO$_4$ | " | " | 3.1 |
| O6 | " | MgSO$_4$ | " | " | 1.7 |
| A6 | Al$_2$O$_3$ | None | 0 | 0.43 | 4.3 |
| P1 | " | FeSO$_4$ | 1.0 Molar | " | 10.1 |
| P2 | " | CoSO$_4$ | " | " | 23.2 |
| P3 | " | NiSO$_4$ | " | " | 16.3 |
| P4 | " | MnSO$_4$ | " | " | 9.7 |
| P5 | " | ZnSO$_4$ | " | " | 12.0 |
| P6 | " | MgSO$_4$ | " | " | 9.7 |
| A7 | Al$_2$O$_3$ | None | 0 | 0.60 | 4.5 |
| Q1 | " | FeSO$_4$ | 1.0 Molar | " | 12.5 |
| Q2 | " | CoSO$_4$ | " | " | 22.8 |
| Q3 | " | NiSO$_4$ | " | " | 22.2 |
| Q4 | " | MnSO$_4$ | " | " | 11.1 |
| Q5 | " | ZnSO$_4$ | " | " | 10.2 |
| Q6 | " | MgSO$_4$ | " | " | 10.1 |
| A8 | Al$_2$O$_3$ | None | 0 | 1.00 | 3.0 |
| R1 | " | FeSO$_4$ | 1.0 Molar | " | 9.7 |
| R2 | " | CoSO$_4$ | " | " | 22.0 |
| R3 | " | NiSO$_4$ | " | " | 26.4 |
| R4 | " | MnSO$_4$ | " | " | 10.5 |
| R5 | " | ZnSO$_4$ | " | " | 6.5 |
| R6 | " | MgSO$_4$ | " | " | 9.6 |

Test data in Table I clearly demonstrate the superiority (in terms of methylcyclopentane conversion) of the invention catalysts, i.e., those prepared from alumina which had been impregnated with a metal salt and contained from 0.37 to 1.00 gram AlCl$_3$ per gram metal salt-impregnated Al$_2$O$_3$, over the corresponding AlCl$_3$/Al$_2$O$_3$ control catalysts. In addition, the selectivity to cyclohexane (i.e., yield of formed cyclohexane divided by converted methylcyclopentane × 100) attained with these invention catalysts generally ranged from about 92% to about 98% whereas the selectivity to cyclohexane attained with catalysts outside the scope of this invention generally was less than 90%.

EXAMPLE III

This example illustrates the use of select catalyst materials described in Example I for the isomerization/disproportionation of n-pentane and isopentane (2-methylbutane), essentially in accordance with the procedure described in Example II (except that n- and isopentane were used as feed hydrocarbons). Test data for n-pentane conversion are summarized in Table II, and test data for isopentane conversion are summarized in Table III.

TABLE II

| Employed Catalyst | Grams AlCl$_3$ per Gram Treated Alumina | Liquid Product Composition (Weight-%) | | | | % Conversion of n-Pentane |
|---|---|---|---|---|---|---|
| | | n-Pentane | Isopentane | C$_4$ Alkanes | C$_6$$^+$ Alkanes | |
| A1[1] | 0.25 | 94.5 | 4.3 | 0.6 | 0.6 | 5.5 |
| B1[2] | " | 71.8 | 17.9 | 3.3 | 7.1 | 28.2 |
| C1[2] | " | 92.1 | 5.2 | 1.3 | 1.3 | 7.9 |
| D1[2] | " | 78.3 | 13.3 | 3.9 | 4.5 | 21.7 |
| E1[2] | " | 96.6 | 2.1 | 0.6 | 0.7 | 3.4 |
| A2[1] | 0.37 | 92.9 | 5.2 | 0.8 | 1.1 | 7.1 |
| B2[2] | " | 66.9 | 21.2 | 5.0 | 6.8 | 33.1 |
| C2[2] | " | 56.8 | 22.6 | 8.5 | 10.1 | 43.2 |
| D2[2] | " | 47.3 | 27.4 | 12.4 | 12.9 | 52.7 |
| E2[2] | " | 69.2 | 17.9 | 6.1 | 6.8 | 30.8 |
| F2[2] | " | 58.2 | 23.4 | 9.3 | 9.1 | 41.8 |
| A3[1] | 0.43 | 91.8 | 6.0 | 1.0 | 1.2 | 8.2 |
| C3[2] | " | 63.3 | 20.4 | 7.0 | 9.3 | 36.7 |
| D3[2] | " | 42.1 | 29.1 | 13.6 | 15.2 | 57.9 |
| E3[2] | " | 42.4 | 29.9 | 13.6 | 14.2 | 57.6 |
| F3[2] | " | 43.5 | 29.9 | 12.2 | 14.4 | 56.5 |
| A4[1] | 0.50 | 90.4 | 6.5 | 1.6 | 1.5 | 9.6 |
| B4[2] | " | 64.0 | 21.6 | 4.8 | 9.6 | 36.0 |
| C4[2] | " | 43.9 | 29.1 | 9.5 | 17.5 | 56.1 |
| D4[2] | " | 45.9 | 29.0 | 12.0 | 13.1 | 54.1 |
| E4[2] | " | 46.3 | 28.8 | 7.4 | 17.6 | 53.7 |
| F4[2] | " | 49.6 | 27.0 | 8.8 | 14.6 | 50.4 |
| A5[1] | 0.25 | 78.8 | 14.6 | 3.1 | 3.5 | 21.2 |
| O3[3] | " | 92.5 | 4.4 | 1.4 | 1.7 | 7.5 |
| A6[1] | 0.43 | 74.3 | 15.5 | 4.6 | 5.6 | 25.7 |
| P3[3] | " | 64.6 | 20.6 | 8.0 | 6.8 | 35.4 |
| A7[1] | 0.60 | 68.7 | 22.4 | 4.4 | 4.5 | 31.3 |
| Q3[3] | " | 50.6 | 30.3 | 8.7 | 10.4 | 49.4 |
| A8[1] | 1.0 | 67.7 | 24.2 | 3.8 | 4.3 | 32.3 |

TABLE II-continued

| Employed Catalyst | Grams AlCl$_3$ per Gram Treated Alumina | Liquid Product Composition (Weight-%) | | | | % Conversion of n-Pentane |
|---|---|---|---|---|---|---|
| | | n-Pentane | Isopentane | C$_4$ Alkanes | C$_6$+Alkanes | |
| R3[3] | " | 56.8 | 26.9 | 6.6 | 9.7 | 43.2 |

[1]Catalysts A1–A8 were AlCl$_3$/Al$_2$O$_3$ control catalysts
[2]Catalyst B-B4, C-C4, D-D4, E1-E4 and F1-F4 were prepared from CuSO$_4$-impregnated Al$_2$O$_3$
[3]Catalysts O3, P3, Q3, and R3 were prepared from NiSO$_4$-impregnated Al$_2$O$_3$.

TABLE III

| Employed Catalyst | Grams AlCl$_3$ per Gram Treated Alumina | Liquid Product Composition (Weight-%) | | | | % Conversion of n-Pentane |
|---|---|---|---|---|---|---|
| | | n-Pentane | Isopentane | C$_4$ Alkanes | C$_6$+Alkanes | |
| A1[1] | 0.25 | 97.3 | 0.8 | 1.0 | 0.9 | 2.7 |
| B1[2] | " | 63.5 | 5.1 | 5.9 | 25.5 | 36.5 |
| C1[2] | " | 89.8 | 2.4 | 1.5 | 6.3 | 10.2 |
| D1[2] | " | 61.7 | 5.0 | 3.8 | 5.0 | 38.3 |
| E1[2] | " | 96.5 | 1.1 | 0.7 | 1.7 | 3.5 |
| A2[1] | 0.37 | 96.3 | 1.3 | 1.0 | 1.4 | 3.7 |
| B2[2] | " | 80.4 | 5.1 | 5.2 | 9.2 | 19.6 |
| C2[2] | " | 61.6 | 5.9 | 13.8 | 18.7 | 38.4 |
| D2[2] | " | 42.8 | 6.9 | 24.9 | 25.4 | 57.2 |
| E2[2] | " | 58.0 | 6.5 | 17.8 | 17.7 | 42.0 |
| F2[2] | " | 40.3 | 8.5 | 17.0 | 34.2 | 59.7 |
| A3[1] | 0.43 | 96.0 | 1.2 | 1.6 | 1.2 | 4.0 |
| C3[2] | " | 73.4 | 6.7 | 7.5 | 12.4 | 26.6 |
| D3[2] | " | 45.5 | 7.5 | 21.6 | 25.4 | 54.5 |
| E3[2] | " | 35.3 | 7.9 | 28.3 | 28.5 | 64.7 |
| F3[2] | " | 40.2 | 8.1 | 24.9 | 26.8 | 59.8 |
| A4[1] | 0.50 | 95.3 | 1.4 | 1.9 | 1.3 | 4.7 |
| B4[2] | " | 75.7 | 6.4 | 1.6 | 16.3 | 24.3 |
| C4[2] | " | 48.5 | 8.0 | 15.3 | 8.0 | 51.5 |
| D4[2] | " | 40.6 | 9.8 | 4.3 | 45.3 | 59.4 |
| E4[2] | " | 58.2 | 7.3 | 9.9 | 24.6 | 41.8 |
| F4[2] | " | 46.1 | 7.9 | 20.9 | 25.1 | 53.9 |
| A5[1] | 0.25 | 84.9 | 4.1 | 4.3 | 6.7 | 15.1 |
| O3[3] | " | 88.5 | 3.4 | 3.0 | 5.1 | 11.6 |
| A6[1] | 0.43 | 87.4 | 4.3 | 3.2 | 5.0 | 12.6 |
| P3[3] | " | 84.2 | 5.5 | 4.3 | 6.0 | 15.8 |
| A7[1] | 0.60 | 87.0 | 5.2 | 2.7 | 5.0 | 13.0 |
| Q3[3] | " | 85.0 | 6.3 | 2.5 | 6.2 | 15.0 |
| A8[1] | 1.0 | 91.4 | 3.5 | 2.1 | 2.9 | 8.6 |
| R3[3] | " | 81.7 | 6.8 | 3.4 | 8.1 | 18.3 |

[1]Catalysts A1–A8 were AlCl$_3$/Al$_2$O$_3$ control catalysts
[2]Catalyst B-B4, C-C4, D-D4, E1-E4 and F1-F4 were prepared from CuSO$_4$-impregnated Al$_2$O$_3$
[3]Catalysts O3, P3, Q3, and R3 were prepared from NiSO$_4$-impregnated Al$_2$O$_3$.

Test data in Tables II and III demonstrate that the catalyst materials which has been prepared from CuSO$_4$- and NiSO$_4$-pretreated alumina and contained 0.37–1.0 grams ACl$_3$ per gram treated alumina support were more effective as alkane conversion catalysts than the corresponding AlCl$_3$/Al$_2$O$_3$ control catalysts. Preliminary test data regarding the use of the other catalyst materials described in Example I indicated that these materials were also quite active as alkane conversion (i.e., isomerimation/disproportionation) catalysts and were frequently (but not always) more effective than the corresponding AlCl$_3$/Al$_2$O$_3$ control catalysts.

EXAMPLE IV

This example illustrates the preparation of catalyst compositions substantially in accordance with the procedure described in Example I, except an HCl-treatment step was carried out after the impregnation of alumina with a metal salt and calcination and before the refluxing with AlCl$_3$ and CCl$_4$. In control catalysts, the metal impregnation step had been omitted.

Catalyst S1 was prepared by soaking 20–40 mesh alumina particles (described in Example I) with an aqueous 1.0 molar CuSO$_4$ solution, followed by filtering, drying in a vacuum oven, (50° C./0.1 torr/2 hours), and calcining in a dry N$_2$ atmosphere at 500° C. for 2 hours. Thereafter, 1.5 grams of calcined, CuSO$_4$-impregnated alumina particles were heated with 0.896 g AlCl$_3$ and 30 mL dry CCl$_4$ under reflux conditions for about 18 hours, followed by drying under vacuum conditions (for about 4 hours).

Catalyst S2 was prepared essentially in the same manner as Catalyst S1, except that the dry CuSO$_4$-impregnated alumina particles were calcined in N$_2$ at 730° C. for 2 hours, the calcined particles were then heated in a gaseous stream of HCl-N$_2$ (volume-% of HCl: 5%) at 730° C. for 7 hours, and the hot, HCl-treated particles were allowed to cool to room temperature in the HCl/N$_2$ gas stream, before the refluxing with 0.896 g AlCl$_3$ and 30 mL CCl$_4$ (as described for S1) was carried out.

Catalyst T1 was prepared essentially in accordance with the procedure for preparing Catalyst S1, except that a 2.0 molar aqueous CuCl$_2$ solution was employed (in lieu of the CuSO$_4$ solution), and the calcining in N$_2$ was carried out at 680°–700° C. for 2 hours.

Catalyst T2 was prepared essentially in accordance with the procedure for Catalyst T1, except that the calcined CuCl$_2$-impregnated alumina particles were heated in a HCl/N$_2$ gas stream (containing 5 volume-% HCl) at 680°–700° C. for 2 hours and then allowed to cool in the HCl-N$_2$ gas stream, before the refluxing with 0.896 g AlCl$_3$ and 30 mL CCl$_4$ was carried out.

Catalyst U1 was prepared essentially in the same manner as Catalyst S1, except that a 1.0 molar aqueous CoSO$_4$ was employed (in lieu of the CuSO$_4$ solution), the calcining in $N_2$ was carried out at about 700° C. for 2 hours, and 0.640 g $AlCl_3$ was used during the refluxing with 1.5 g $CoSO_4$-impregnated $Al_2O_3$ in $CCl_4$.

Catalyst U2 was prepared essentially in accordance with the procedure for Catalyst U1, except that the calcined $CoSO_4$-impregnated alumina particles were heated in a $HCl/N_2$ gas stream (containing 5 volume-% HCl) at about 700° C. for 2 hours and then allowed to cool in this gas stream, before the refluxing with 0.640 g $AlCl_3$ and 30 mL $CCl_4$ was carried out.

Catalyst V1 was prepared essentially in the same manner as Catalyst T1, except that a 2.0 molar aqueous $CoCl_2$ was employed (in lieu of the $CuCl_2$ solution).

Catalyst V2 was prepared essentially in accordance with the procedure for Catalyst V1, except that the calcined, $CoCl_2$-impregnated alumina particles were heated in a $HCl/N_2$ gas stream (containing 5 volume-% HCl) at about 700° C. for 2 hours and then allowed to cool in this gas stream, before the refluxing with 0.64 g $AlCl_3$ and 30 mL $CCl_4$ was carried out.

Catalyst W1 was prepared essentially in the same manner as Catalyst S1, except that a 1.0 molar aqueous $NiSO_4$ solution was employed (in lieu of the $CuSO_4$ solution), the calcining in $N_2$ was carried out at about 700° C. for 2 hours, and 0.640 g $AlCl_3$ was used during the refluxing in with 1.5 g $NiSO_4$-impregnated $Al_2O_3$ in $CCl_4$.

Catalyst W2 was prepared essentially in accordance with the procedure for Catalyst W1, except that the calcined $NiSO_4$-impregnated alumina particles were heated in a $HCl/N_2$ gas stream (containing 5 volume-% HCl) at about 700° C. for 2 hours, and then allowed to cool in this gas stream, before the refluxing with 0.64 g $AlCl_3$ and 30 mL $CCl_4$.

Catalyst X1 was prepared essentially in the same manner as Catalyst T1, except that a 2.0 molar aqueous $NiCl_2$ was employed (in lieu of the $CuCl_2$ solution).

Catalyst X2 was prepared essentially in accordance with the procedure for Catalyst X2, except that the calcined, $NiCl_2$-impregnated alumina particles were heated in a $HCl/N_2$ gas stream (containing 5 volume-% HCl) at about 700° C. for 2 hours and then allowed to cool in this gas stream, before the refluxing with 0.896 g $ACl_3$ and 30 mL $CCl_4$ was carried out.

EXAMPLE V

This example illustrates the beneficial effect of the HCl-treatment of metal salt-impregnated alumina (before the heating with $AlCl_3$ and $CCl_4$). The preparation of the employed catalysts has been described in Example IV. The thus-prepared catalysts were tested alkylation tests essentially in accordance with the procedure described in Examples II and III. Test results are summarized in Table IV.

TABLE IV

| Employed Catalyst | Catalyst Preparation Method | | HCl Pre-Treatment of Alumina | Feed Hydrocarbon | % Conversion of Feed Hydrocarbon |
|---|---|---|---|---|---|
| | Metal Salt used to Treat Alumina Support | Conc. of Metal Salt in Treating Solution | | | |
| S1 | $CuSO_4$ | 1.0 Molar | No | n-Pentane | 31.4 |
| S2 | " | " | Yes | " | 48.5 |
| S1 | " | " | No | Isopentane | 32.0 |
| S2 | " | " | Yes | " | 52.8 |
| S1 | " | " | No | MCP[1] | 27.1 |
| S2 | " | " | Yes | " | 46.1 |
| T1 | $CuCl_2$ | 2.0 Molar | No | n-Pentane | 31.1 |
| T2 | " | " | Yes | " | 45.7 |
| T1 | " | " | No | Isopentane | 31.7 |
| T2 | " | " | Yes | " | 47.4 |
| T1 | " | " | No | MCP[1] | 23.7 |
| T2 | " | " | Yes | " | 34.8 |
| U1 | $CoSO_4$ | 1.0 Molar | No | n-Pentane | 23.0 |
| U2 | " | " | Yes | " | 30.1 |
| U1 | " | " | No | Isopentane | 12.7 |
| U2 | " | " | Yes | " | 24.8 |
| U1 | " | " | No | MCP[1] | 16.3 |
| U2 | " | " | Yes | " | 23.5 |
| V1 | $CoCl_2$ | 2.0 Molar | No | n-Pentane | 19.3 |
| V2 | " | " | Yes | " | 24.7 |
| V1 | " | " | No | Isopentane | 12.4 |
| V2 | " | " | Yes | " | 19.1 |
| V1 | " | " | No | MCP[1] | 15.8 |
| V2 | " | " | Yes | " | 23.0 |
| W1 | $NiSO_4$ | 1.0 Molar | No | n-Pentane | 19.9 |
| W2 | " | " | Yes | " | 26.7 |
| W1 | " | " | No | Isopentane | 14.8 |
| W2 | " | " | Yes | " | 25.8 |
| W1 | " | " | No | MCP[1] | 15.6 |
| W2 | " | " | Yes | " | 20.4 |
| X1 | $NiCl_2$ | 2.0 Molar | No | n-Pentane | 18.1 |
| X2 | " | " | Yes | " | 23.9 |
| X1 | " | " | No | Isopentane | 13.5 |
| X2 | " | " | Yes | " | 24.5 |
| X1 | " | " | No | MCP[1] | 15.3 |
| X2 | " | " | Yes | " | 20.7 |

Notes:
(1) MCP means methylcyclopentane
(2) MCP was converted to cyclohexane at a selectivity of over 90%
(3) Product of n-pentane conversoin contained isopentane, $C_4$ and $C_6+$ alkanes (see Table II)
(4) Product of isopentane conversion contained n-pentane, $C_4$ and $C_6+$ alkanes (see Table III).

Test data summarized in Table IV clearly demonstrate the superiority of the catalysts the preparation of which comprised HCl pretreatment of metal salt-impregnated alumina (Catalysts S2, T2, U2, V2, W2 and X2) over the corresponding catalysts which were prepared without the HCl pretreatment (Catalysts S1, T1, U1, V1, W1 and X1).

Reasonable variations, modifications and adaptations for various usages and conditions can be made within the scope of the disclosure and the appended claims, without departing from the scope of this invention.

That which is claimed is:

1. A method of preparing a composition of matter consisting essentially of the steps of:
   (1) impregnating alumina having a surface area of at least about 40 m²/g with a solution of at least one metal salt selected from the group consisting of copper(II) sulfate, iron(II) sulfate, cobalt(II) sulfate, nickel(II) sulfate, manganese(II) sulfate, zinc sulfate and magnesium sulfate;
   (2) calcining the material obtained in step (1) for a period of at least 0.5 hour at a temperature of about 400°–750° C.;
   (3) heating for a period of at least one hour, at a temperature in the range of about 40° C. to about 90° C. and in substantial absence of water, a mixture consisting essentially of the calcined material obtained in step (2), aluminum chloride and at least one chlorinated hydrocarbon selected from the group consisting of dichloromethane, chloroform, carbon tetrachloride, 1,1-dichloroethane, 1,2-dichloroethane, 1,1,1-trichloroethane, 1,1-dichloropropane, 2,2-dichloropropane, 1-chlorobutane and 2-chloro-2-methylbutane, wherein the weight ratio of $AlCl_3$ to said calcined material obtained in step (2) is at least about 0.35:1; and
   (4) separating the solid material contained in the reaction mixture formed in step (3) from said at least one chlorinated hydrocarbon under a dry gas atmosphere.

2. A method in accordance with claim 1, wherein said alumina used in step (1) has a surface area of about 200–500 m²/g and a particle size of about 20–200 mesh, and said solution contains about 0.1–3.0 mole/l of said at least one metal salt.

3. A method in accordance with claim 1, wherein said at least one chlorinated hydrocarbon used in step (3) is carbon tetrachloride.

4. A method in accordance with claim 3, wherein said at least one metal salt is selected from the group consisting of $CuSO_4$, $CoSO_4$ and $NiSO_4$.

5. A method in accordance with claim 3, wherein step (3) is carried out under an inert gas atmosphere at a temperature of about 70°–80° C. for a time period of about 4–120 hours.

6. A method in accordance with claim 3, wherein said weight ratio of $AlCl_3$ to said calcined material employed in step (3) is about 0.37:1 to about 1.0:1.

7. A method in accordance with claim 1, wherein step (4) is carried out by filtering the reaction mixture obtained in step (3) and drying the obtained solid filter cake under a dry inert gas atmosphere.

8. A method of preparing a composition of matter consisting essentially of the steps of:
   (1) impregnating alumina having a surface area of at least about 40 m²/g with a solution of at least one metal salt selected from the group consisting of copper(II) sulfate, iron(II) sulfate, cobalt(II) sulfate, nickel(II) sulfate, manganese(II) sulfate, zinc sulfate and magnesium sulfate;
   (2) calcining the material obtained in step (1) for a period of at least one hour at a temperature of about 400°–750° C.;
   (2a) contacting the calcined material obtained in step (2) with dry gaseous hydrogen chloride at a temperature of about 600°–750° C. for at least about 10 minutes;
   (3) heating for a period of at least one hour, at a temperature in the range of about 40° C. to about 90° C. and in substantial absence of water, a mixture consisting essentially of the calcined material obtained in step (2a), aluminum chloride and at least one chlorinated hydrocarbon selected from the group consisting of dichloromethane, chloroform, carbon tetrachloride, 1,1-dichloroethane, 1,2-dichloroethane, 1,1,1-trichloroethane, 1,1-dichloropropane, 2,2-dichloropropane, 1-chlorobutane and 2-chloro-2-methylbutane, wherein the weight ratio of $AlCl_3$ to said calcined material obtained in step (2a) is at least about 0.35:1; and
   (4) separating the solid material contained in the reaction mixture formed in step (3) from said at least one chlorinated hydrocarbon under a dry gas atmosphere.

9. A method in accordance with claim 5, wherein said alumina used in step (1) has a surface area of about 200–500 m²/g and a particle size of about 20–200 mesh, and said solution contains about 0.1–3.0 mole/l of said at least one metal salt.

10. A method in accordance with claim 5, wherein said at least on chlorinated hydrocarbon used in step (3) is carbon tetrachloride.

11. A method in accordance with claim 10, wherein said at least one metal salt is selected from the group consisting of $CuSO_4$, $CoSO_4$ and $NiSO_4$.

12. A method in accordance with claim 10, wherein step (3) is carried out under an inert gas atmosphere at a temperature of about 70°–80° C. for a time period of about 4–120 hours.

13. A method in accordance with claim 10, wherein step (2a) is carried out for about 1–10 hours with a dry gaseous mixture comprising 4–60 volume-% HCl.

14. A method in accordance with claim 10, wherein step (3) is carried out under an inert gas atmosphere at a temperature of about 70°–80° C. for a time period of about 4–120 hours.

15. A method in accordance with claim 10, wherein said weight ratio of $AlCl_3$ to said calcined material employed in step (3) is about 0.37:1 to about 1.0:1.

16. A method in accordance with claim 8, wherein step (4) is carried out by filtering the reaction mixture obtained in step (3) and drying the obtained solid filter cake under a dry inert gas atmosphere.

17. A composition of matter obtained by the method of claim 1.

18. A composition of matter obtained by the method of claim 6.

19. A composition of matter obtained by the method of claim 8.

20. A composition of matter obtained by the method of claim 15.

* * * * *

UNITED STATES PATENT AND TRADEMARK OFFICE
CERTIFICATE OF CORRECTION

PATENT NO. : 5,358,919

DATED : October 25, 1994

INVENTOR(S) : An-hsiang Wu

It is certified that error appears in the above-identified patent and that said Letters Patent is hereby corrected as shown below:

Claim 9, column 16, line 28, delete "5" and substitute --- 8 --- therefor.

Claim 10, column 16, line 33, delete "5" and substitute --- 8 --- therefor.

Signed and Sealed this

Third Day of January, 1995

Attest:

BRUCE LEHMAN

Attesting Officer

Commissioner of Patents and Trademarks